United States Patent [19]

O'Rourke

[11] 4,377,877
[45] Mar. 29, 1983

[54] POWER DRIVEN ROTARY TOOTHBRUSH WITH AUTOMATIC FLOSSING MEANS

[76] Inventor: James L. O'Rourke, 6351 Memorial, Detroit, Mich. 48228

[21] Appl. No.: 304,805

[22] Filed: Sep. 23, 1981

Related U.S. Application Data

[63] Continuation-in-part of Ser. No. 110,389, Jan. 8, 1980, Pat. No. 4,304,023, which is a continuation-in-part of Ser. No. 898,645, Apr. 12, 1978, Pat. No. 4,181,997.

[51] Int. Cl.³ .............................................. A46B 13/02
[52] U.S. Cl. ............................................ 15/4; 15/23; 15/DIG. 5
[58] Field of Search ...................... 15/22–27, 15/110, 111, 159 A, 167 R, 179, 181, 4, DIG. 5

[56] References Cited

U.S. PATENT DOCUMENTS

| | | | |
|---|---|---|---|
| 1,860,894 | 5/1932 | Lieux | 15/23 |
| 2,840,837 | 7/1958 | Gustems | 15/23 |
| 3,015,833 | 1/1962 | Gilet | 15/23 |
| 3,103,679 | 9/1963 | Clemens | 15/167 R |

FOREIGN PATENT DOCUMENTS

| | | | |
|---|---|---|---|
| 110160 | 4/1900 | Fed. Rep. of Germany | 15/23 |
| 1129650 | 9/1956 | France | 15/23 |

*Primary Examiner*—Edward L. Roberts
*Attorney, Agent, or Firm*—Barnes, Kisselle, Raisch, Choate, Whittemore & Hulbert

[57] ABSTRACT

A tooth-brushing device comprising a brushing unit having a pair of counterrotating shafts, with bristles projecting radially outwardly from each shaft. The bristles are arranged in a series of clusters spaced from one another along the length of each shaft. Preferably, the clusters of bristles are spaced apart a distance approximately the width of a tooth. Some of the bristles may be longer than others, bristles of differing diameter may be used, and special flossing units are also disclosed.

13 Claims, 10 Drawing Figures

POWER DRIVEN ROTARY TOOTHBRUSH WITH AUTOMATIC FLOSSING MEANS

REFERENCE TO RELATED APPLICATION

This application is a continuation-in-part of my prior co-pending application Ser. No. 110,389 filed Jan. 8, 1980, now U.S. Pat. No. 4,304,023 which is a continuation-in-part of my prior application Ser. No. 898,645 filed Apr. 12, 1978, now U.S. Pat. No. 4,181,997.

This invention relates generally to toothbrushes and refers more particularly to a toothbrush having bristles projecting from a pair of power driven shafts.

BACKGROUND AND SUMMARY OF THE INVENTION

Toothbrushes of the rotary, power driven type, of which I am aware, having the bristles uniformly distributed along the length of each shaft. An example of one such toothbrush is shown in U.S. Pat. No. 2,285,865. One of the problems with toothbrushes of this type is that they do not brush satisfactorily between the teeth.

I have discovered that by arranging the bristles in clusters along the length of each shaft, and preferably by spacing the clusters apart a distance approximately the width of a tooth, much more effective brushing between the teeth, where most cavities originate, can be achieved.

More effective brushing between the teeth can also be achieved if some bristles are no longer than others, if differing diameter bristles are used, and if special flossing units are employed, as will become apparent as the following description proceeds, especially when considered with the accompanying drawings.

DETAILED DESCRIPTION

Figure 1:
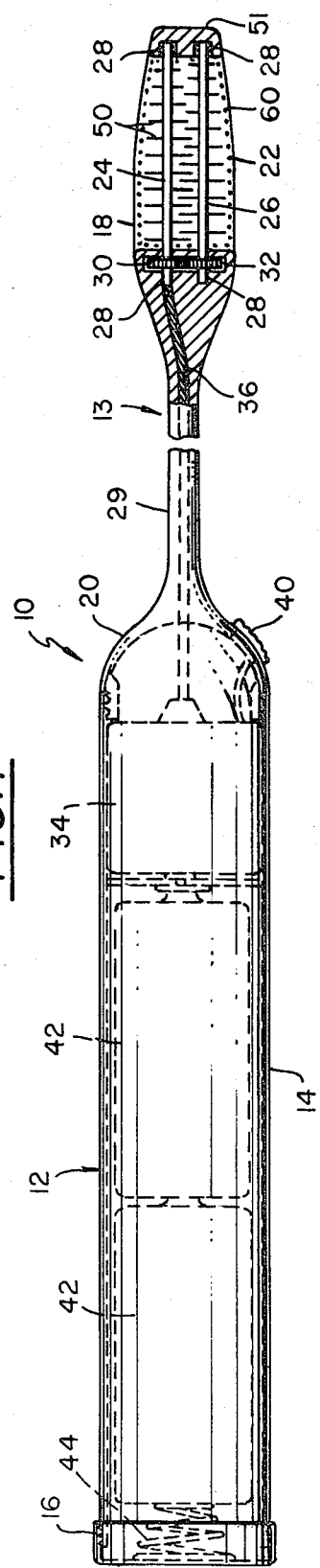
FIG. 1 is an elevational view, with parts in section, of a toothbrush constructed in accordance with my invention.
Figure 2:
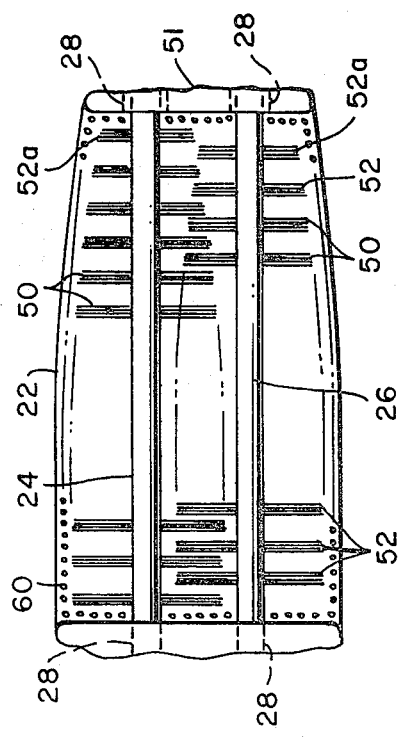
FIG. 2 is an enlarged fragmentary view of a portion of FIG. 1.

Referring now more particularly to the drawings and especially FIGS. 1 and 2 thereof, the toothbrush 10 comprises a body 12 and a brushing unit 13.

The body 12 comprises an elongated open-ended cylindrical tube 14 having a cap 16 threaded on and closing one end. The brushing unit has a head 18 at one end and a cap portion 20 at the opposite end threaded onto the end of the tube 14 opposite cap 16.

The head 18 of the brushing unit has an elongated rear wall 22, along the front side of which extends a pair of shafts 24 and 26. These shafts 24 and 26 are rotatably supported in laterally spaced, parallel relation to each other by journals 28 at opposite ends of the rear wall 22. Gears 30 and 32 secured to the respective shafts mesh with one another so as to constrain the shafts to rotate in opposite directions.

Rotation of the shafts is accomplished by means of an electric motor 34 in the body 12 of the toothbrush which when operated drives a flexible shaft 36 extending through a passage in the cap portion 20 and midportion 29 and connected to the shaft 24. The direction of motor rotation is such as to cause the shafts to rotate in directions to brush the teeth away from the gums. There is an on-off switch 40 mounted externally on the cap portion 20 of the brushing unit in a position for convenient manual operation to turn the electric motor on or off, as desired. The motor 34 is energized by any suitable means, in this instance by dry-cell batteries 42 contained within the body 12 and held in electrical contact with one another and with the motor by a coil spring 44 compressed by the cap 16 against one end of one of the batteries.

A series of flexible bristles 50 project radially outwardly from each of the shafts 24 and 26. The bristles 50 are arranged in a series of clusters or groups 52 spaced from one another along the length of each shaft. There are a plurality of bristles in each cluster distributed in a circular array about the shaft axis and projecting radially outwardly therefrom. The bristles do not contact the rear wall 22 when they rotate. The clusters on each shaft are spaced apart a distance which may vary but preferably, as shown, approximates the width of a single human tooth. The clusters of bristles on each shaft are staggered with respect to the clusters of bristles on the other shaft. The shafts are spaced close enough together so that the clusters of bristles on each shaft extend into the spaces between the clusters of bristles on the other shaft. A compact structure is thus provided which fits easily into the mouth. However, the shaft spacing and bristle length is such that the bristles on one shaft do not touch the other shaft.

The bristles near the end 51 of the head 18 of the toothbrush are progressively shorter in a direction toward that end, producing a taper as clearly shown in the drawings. The purpose of this is to enable more convenient brushing of the back teeth. Thus in FIG. 2 the clusters of bristles 52a on both shafts at the end 51 of the head of the toothbrush are noticeably shorter than those at the opposite end, to an extent that the bristles in each cluster 52a do not quite extend into the adjacent space between the clusters of bristles on the other shaft, although the staggered relation of the clusters of bristles on the two shafts exists throughout the full length of both shafts.

FIG. 2 shows a construction in which all of the bristles in each cluster are of the same length throughout a full 360° around the shaft. These bristles are preferably of uniform flexibility and will brush the teeth and will also get in between the teeth with a sweeping action. Brushing between the teeth, where most cavities originate, is very important. The spacing and distribution of the bristles into clusters enables more effective brushing between the teeth.

Figure 3:
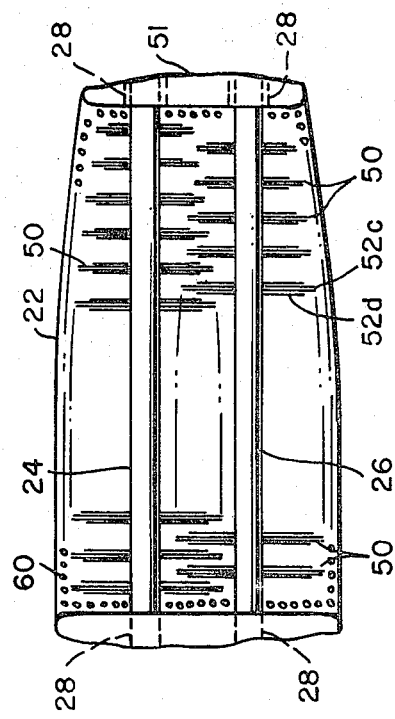
FIG. 3 is similar to FIG. 2 but shows a modification.

FIG. 3 shows a modification in which some of the bristles 52c in each cluster are longer than others 52d. The longer bristles are believed to be more effective in brushing between the teeth and the shorter bristles are believed to be more effective in brushing the surfaces of the teeth. Preferably the longer bristles are more flexible than the shorter bristles.

A line of bristles 60 extend outwardly from the rear wall 22 of the head completely around the clusters of bristles on both shafts to reduce spray produced by the rotation of the shafts. The bristles 60 extend at right angles to a plane containing the longitudinal axes of the two shafts.

Figure 4:
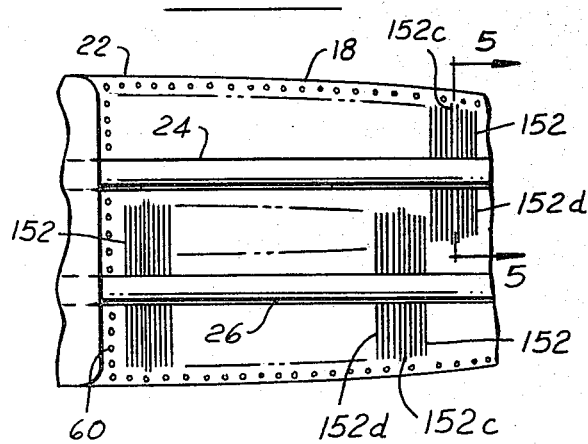
FIG. 4 shows a modification of a portion of FIG. 1.
Figure 5:
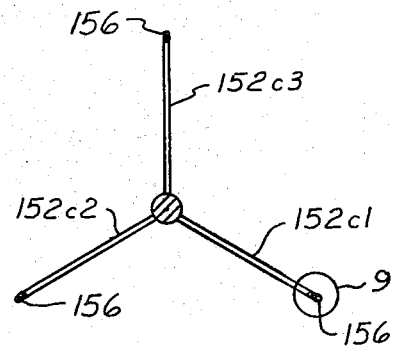
FIG. 5 is a view on the line 5—5 in FIG. 4.

FIGS. 4 and 5 show a further modification. As in FIG. 3, the bristles in FIG. 4 are arranged in a series of clusters or groups 152, with the clusters of bristles on each shaft staggered with respect to the clusters of bristles on the other shaft. Some of the bristles 152c in each cluster are longer than others 152d. As before stated, these longer bristles are believed to be more effective in brushing between the teeth and the shorter bristles more effective in brushing the surfaces of the teeth. Also as in the previous embodiment, the longer bristles are more flexible than the shorter bristles.

FIGS. 4 and 5 differ from FIG. 3 essentially only in the thickness or diameter of the longer bristles 152c and the hardened coating on the ends thereof. As shown in FIG. 5, in which only three of the longer bristles are shown, one designated 152c1 is of relatively large diameter, another designated 152c2 is of an intermediate diameter and the third designed 152c3 is of relatively small diameter. The purpose of varying the diameter of the longer bristles is to achieve more effective brushing between the teeth no matter what the spacing between the teeth may be. Thus, the intermediate diameter bristles 152c2 are adapted to brush between teeth spaced apart a normal or average distance. The smaller diameter bristles 152c3 are adapted to brush between the more closely spaced teeth, while the larger diameter bristles 152c1 are adapted to brush between the more widely spaced teeth.

It will be understood that while only three of the longer bristles are shown in FIG. 5, actually a great many of the longer bristles may be employed, radiating out from the shaft in the same plane indicated by section line 5—5 and being of varying diameter or thickness. The arrangement of the longer bristles may vary, but preferably they will vary in sequence from small to medium to large diameter circumferentially around the shaft. In other words, proceeding circumferentially around the shaft the bristles in sequence will be small, medium, large, small, medium, large, etc. throughout the full 360°.

FIG. 5 shows each of the longer bristles 152c as being provided with a thin, smooth, hardened coating 156 of a suitable plastic or like material. The purpose of this coating is to protect the tip from wear, by reason of its hardness, and by reason of its smoothness to prevent injury to the gums of the person using the toothbrush.

It will be understood that the several clusters of bristles on each shaft shown in FIG. 4 may each have a plurality of the longer bristles of varying diameter, similar to the ones illustrated and described in connection with FIG. 5.

Except as above described, the construction of FIGS. 4 and 5 may otherwise be like that of FIGS. 1–3.

Figure 6:
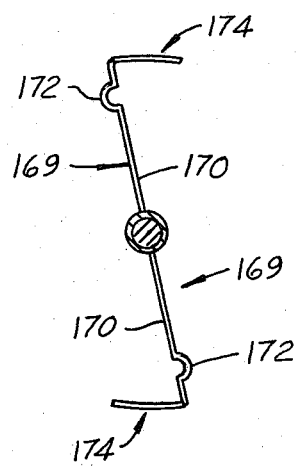

FIG. 6 shows a further modification in which instead of employing longer bristles to brush between the teeth, flossing units 169 are substituted. Each flossing unit 169 will be placed in a cluster or bristles in the same location where the longer bristles shown in FIG. 5 where placed, that is in the plane indicated by the section line 5—5 in FIG. 4. Each flossing unit 169 comprises a flexible support 170 which is a bristle-like member that may have a spring section 172 intermediate its length. This support projects outwardly from the shaft in a radial direction. A flossing member 174 has one end connected to the outer end of the support 170 and extends circumferentially therefrom. The radial support 170 corresponds in length generally to the longer bristles of FIG. 5, that is it extends radially outward beyond the shorter bristles 152d, and hence the flossing member is disposed radially outward beyond the shorter bristles 152d.

Figure 8:
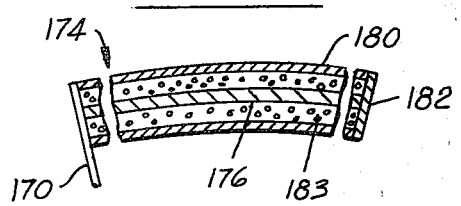
FIG. 8 is an enlarged sectional view of a portion of FIG. 6.
Figure 9:
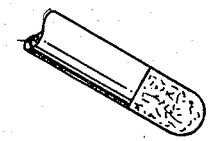
FIG. 9 is an enlargement of a portion of FIG. 5.

This flossing member 174 comprises a circumferential arm 176 one end of which is attached rigidly to the outer end of the support 170, and a sleeve 180 of flossing material rotatably supported on the arm. This sleeve 180 is held on the arm 176 against endwise movement by the radial support 170 and an abutment 182 on the free end of the arm. As noted in FIG. 8, there is a space between the arm and the sleeve which may be filled with a suitable cushioning spronge or foam material of rubber, plastic or the like to provide a yielding rotatable support for the sleeve. The spring section 172 provides a yielding, resilient support for the flossing member 174, allowing it to flex in and out across the walls of the teeth with a floating action and into the spaces between adjacent teeth. This same brushing and flossing action will occur, in the opposite plane, when the user brushes the grinding surfaces of the back (molar) teeth.

FIG. 6 shows two flossing units 169 in the same plane 180° apart. If desired any number of such units may be employed.

Figure 7:
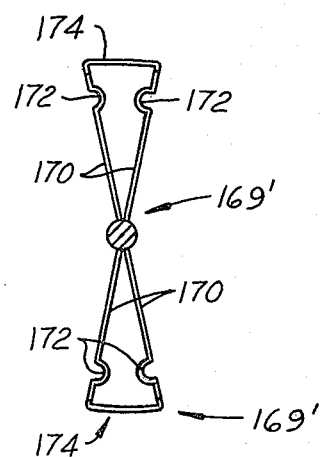
FIGS. 6 and 7 show further modifications.

FIG. 7 shows a further modification which is like FIG. 6, except that an additional radial support 170 is provided, so that the two ends of the circumferential arm of the flossing member 174 are rigidly attached to the outer ends of the respective supports 170. Obviously in this modification the separate abutment 182, employed in FIG. 6, is not needed because its function is performed by one of the radial arms 170. Although FIG. 7 shows two flossing units 169' in the same plane 180° apart, any number of such units may be employed.

It will be understood that each of the several clusters of bristles on each shaft in FIG. 4 may have one or more of the flossing units 169 or one or more of the flossing units 169', or some of each.

Figure 10:
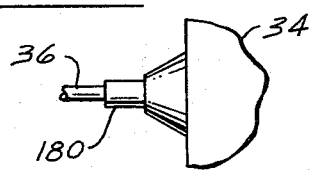
FIG. 10 is a fragmentary view of another modification.

FIG. 10 shows a modification in which an overload or slip clutch 180 is provided between the motor 34 and the flexible drive shaft 36. The clutch protects the parts of the toothbrush from damage and the user from injury in the unlikely event that the shafts 24, 26 or the bristles or flossing units become fouled or snagged.

I claim:

1. A tooth-brushing device comprising a brushing unit having a pair of shafts, means rotatably supporting said shafts in laterally spaced, parallel relation to each other, flexible bristles projecting radially outwardly from said shaft in a circular array about the axis thereof, some of said bristles being longer than others for more effective brushing between the teeth, some of said longer bristles being of larger diameter than others, the small diameter bristles being adapted to brush between the more closely spaced teeth and the larger diameter bristles being adapted to brush between the more widely spaced teeth, and means for counterrotating said shafts in directions to brush the teeth away from the gums.

2. A tooth-brushing device as defined in claim 1, wherein said longer bristles of each shaft project from said shaft in substantially the same plane.

3. A tooth-brushing device as defined in claim 1, wherein said bristles are arranged in a series of clusters spaced from one another along the length of each shaft, there being a plurality of longer bristles in each cluster, some of said longer bristles in each cluster being of larger diameter than others.

4. A tooth-brushing device as defined in claim 3, wherein said longer bristles in each cluster project from the shaft axis in substantially the same plane.

5. A tooth-brushing device as defined in any one of the preceding claims, wherein the tips of said longer bristles have a thin, smooth, hardened coating.

6. A tooth-brushing device comprising a brushing unit having a pair of shafts, means rotatably supporting said shafts in laterally spaced, parallel relation to each other, flexible bristles projecting radially outwardly from said shaft in a circular array about the axis thereof, and flossing units interspaced among said bristles, each flossing unit comprising a flexible radial support, a circumferential flossing member on the outer end of said support, and means for counterrotating said shafts in directions to brush the teeth away from the gums.

7. A tooth-brushing device as defined in claim 6, wherein said flossing member comprises a circumferential arm, and a sleeve of flossing material on said arm.

8. A tooth-brushing device as defined in claim 7, wherein said sleeve is rotatably supported on said arm.

9. A tooth-brushing device as defined in claim 8, including cushioning material between said arm and sleeve.

10. A tooth-brushing device as defined in claim 9, wherein said support is a single flexible member connected to one end of said arm.

11. A tooth-brushing device as defined in claim 9, wherein said support is composed of two flexible members connected to opposite ends of said arm.

12. A tooth-brushing device as defined in claim 10 or 11, wherein said support has a spring section, whereby said flossing member is yieldably, resiliently supported and capable of flexing in and out across the walls of the teeth, or the grinding surface of the molar teeth, with a floating action, and into the spaces between the adjacent teeth.

13. A tooth-brushing device comprising a brushing unit having a support, means movably mounting said support, flexible bristles projecting from said support, and a flossing unit adjacent said bristles, said flossing unit comprising a resilient holder mounted on said support, a flossing member on said holder near the tip of said bristles, and power means for moving said support.

* * * * *